United States Patent
Popescu

(10) Patent No.: US 7,340,029 B2
(45) Date of Patent: Mar. 4, 2008

(54) X-RAY COMPUTED TOMOGRAPHY APPARATUS FOR FAST IMAGE ACQUISITION

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 101 days.

(21) Appl. No.: 11/312,793

(22) Filed: Dec. 20, 2005

(65) Prior Publication Data

US 2006/0159221 A1    Jul. 20, 2006

(30) Foreign Application Priority Data

Dec. 20, 2004   (DE) ............ 10 2004 061 347

(51) Int. Cl.
  *H05G 1/60*   (2006.01)
  *A61B 6/00*   (2006.01)
  *G21K 1/04*   (2006.01)

(52) U.S. Cl. ............ 378/10; 378/151; 378/155

(58) Field of Classification Search ............ 378/7, 378/10, 16, 19, 147, 150, 151, 154, 155, 378/156, 157, 158

See application file for complete search history.

(56) References Cited

U.S. PATENT DOCUMENTS

| 4,158,142 | A |   | 6/1979 | Haimson ............ 378/113 |
| 4,203,036 | A | * | 5/1980 | Tschunt ............ 378/10 |
| 4,352,021 | A |   | 9/1982 | Boyd et al. ............ 378/12 |
| 4,521,900 | A |   | 6/1985 | Rand ............ 378/137 |
| 4,521,901 | A |   | 6/1985 | Rand ............ 378/138 |
| 4,606,061 | A |   | 8/1986 | Ramamurti ............ 378/10 |
| 5,191,600 | A |   | 3/1993 | Vincent et al. ............ 378/10 |
| 5,195,112 | A |   | 3/1993 | Vincent et al. ............ 378/10 |
| 6,243,438 | B1 | * | 6/2001 | Nahaliel et al. ............ 378/19 |
| 6,792,077 | B2 |   | 9/2004 | Rand ............ 378/149 |
| 2005/0111610 | A1 | * | 5/2005 | De Man et al. ............ 378/10 |
| 2006/0023832 | A1 | * | 2/2006 | Edic et al. ............ 378/7 |

* cited by examiner

*Primary Examiner*—Allen C. Ho
(74) *Attorney, Agent, or Firm*—Schiff Hardin LLP

(57) ABSTRACT

An x-ray computed tomography apparatus has a stationary device (3) for generating x-ray radiation from an x-ray focus that moves around the examination volume on a target that at least partially surrounds an examination volume of the apparatus in one plane. From the x-ray focus an x-ray beam is directed through the examination volume onto respective, momentarily opposite detector elements of a stationary x-ray detector that at least partially surrounds the examination volume. One or more shaping elements for influencing one or more beam parameters of the x-ray beam are arranged between the target and the detector elements. One or more of the shaping elements is/are arranged on a carrier frame that can rotate around a system axis in synchronization with the movement of the x-ray focus. The shaping elements rotating with the x-ray focus enable an optimal beam shaping and/or suppression of scatter radiation.

4 Claims, 4 Drawing Sheets

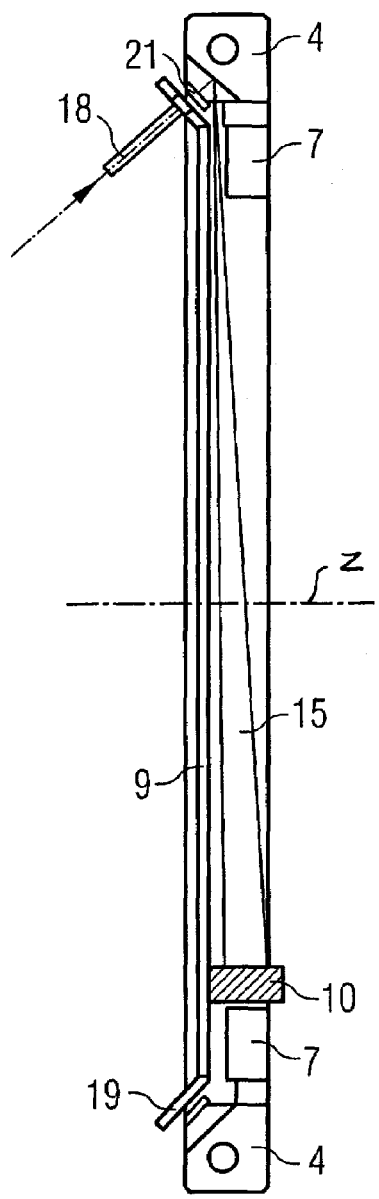
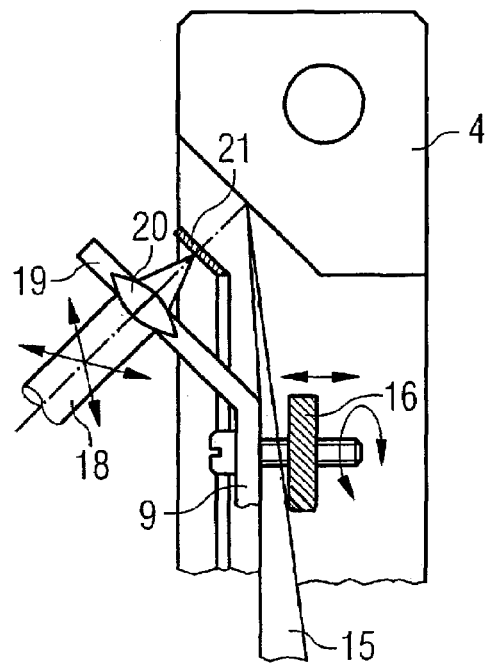

X-RAY COMPUTED TOMOGRAPHY APPARATUS FOR FAST IMAGE ACQUISITION

BACKGROUND OF THE INVENTION

1. Field of the Invention

The present invention concerns an x-ray computed tomography apparatus of the type having a stationary device for generation of x-ray radiation from an x-ray focus that moves around the examination volume on a target that at least partially encloses an examination volume of the apparatus in one plane, wherein an x-ray beam is directed from the focus through the examination volume onto respective, temporarily opposite detector elements of a stationary x-ray detector that at least partially surrounds the examination volume, and wherein one or more shaping elements that influence one or more beam parameters of the x-ray beam are arranged between the target and the detector elements.

2. Description of the Prior Art

Computed tomography systems are used in medical imaging to acquire images of the inside of the body of a patient. A computed tomography apparatus includes, among other things, a device for generating x-ray radiation, an x-ray detector and a patient positioning table with which the examination subject can be moved in the examination volume along a system axis (the z-axis) during the examination. The device for generating x-ray radiation emits an x-ray beam that emanates from an x-ray focus rotating around the examination volume. In examinations, the x-ray beam, which expands in a fan shape perpendicular to the system axis in a slice plane of the examination volume (X-Y plane), penetrates a slice of the examination subject (for example a body slice of a patient) and strikes the detector elements of the x-ray detector opposite the x-ray focus. The angle at which the x-ray beam penetrates the body slice of the patient and, if applicable, the position of the patient positioning table normally continuously vary during the image acquisition with the computed tomography apparatus.

The intensity of the x-rays of the x-ray beam that strikes the x-ray detectors after penetrating the patient is dependent on the attenuation of the x-rays by the patient. Dependent on the intensity of the received x-ray radiation, each detector element of a detector row of the x-ray detector generates a voltage signal that corresponds to a measurement of the global transparency of the body for x-rays from the x-ray tube to the corresponding detector element. A set of voltage signals of the detector elements of a detector row, which represent attenuation data and were acquired for a specific position of the x-ray source relative to the patient, is designated as a projection. A set of projections acquired at various positions during the movement of the x-ray focus around the patient is designated as a scan. The computed tomography apparatus acquires many projections at various positions of the x-ray focus relative to the body of the patient in order to reconstruct an image that corresponds to a two-dimensional slice image of the body of the patient or a three-dimensional image. For acquiring a number of slice images or acquiring a three-dimensional image, a volume scan is implemented that encompasses a number of rotations of the x-ray focus around the examination volume given a feed movement of the patient table in the Z-direction. The prevalent method for reconstruction of a slice image or three-dimensional image from acquired attenuation data is known as filtered back-projection. The image reconstruction is normally implemented with an image computer that obtains the measurement data from the detector elements and further processes the data.

In a computed tomography apparatus of the third generation, the rotating x-ray focus is generated by an x-ray tube that, like the x-ray detector, is attached on a rotary frame that can be rotated around the examination volume. The rotation speed of the rotary frame has been increased in recent years in order to achieve faster scan speeds in the image acquisition. Even higher scan speeds, however, are required for new applications of computed tomography such as, for example, examination of the heart or blood circulation in vessels. In the meantime, for reasons of mechanical stability and safety in computed tomography systems of the third generation, a limit has been reached that no longer allows a distinct increase of the rotation speed of the rotary frame due to the masses that must be moved and the high acceleration forces resulting therefrom.

In a computed tomography apparatus of the fourth generation, the x-ray detector is arranged as a stationary ring around the examination volume such that only the x-ray tube must still be moved with the rotary frame. However, here as well significant forces that limit the maximum rotation speed act on the x-ray tube given a further increase of the rotation speed of the rotary frame.

To avoid this problem, in the meantime computed tomography systems of the fifth generation have become known in which both the device for generating x-ray radiation and the x-ray detector are stationary. In these computed tomography systems a target is used that at least partially encloses the examination volume of the apparatus in one plane. An x-ray focus moving around the examination volume is generated on the target, from which the x-ray radiation emanates. These computed tomography systems thus operate entirely without a mechanically-moving x-ray tube. The target extends either completely around the examination volume or at least over an angle of more than 180° around the examination volume. In the same manner, the x-ray detector encloses the examination volume either completely or over an angle of at least 180° and is arranged such that an x-ray beam emanating from the x-ray focus strikes (through the examination volume) on respective, momentarily opposite detector elements of the stationary x-ray focus.

For example, U.S. Pat. Nos. 4,158,142 and 4,352,021 disclose computed tomography systems of the fifth generation in which the target and the x-ray detector each completely surround the examination volume or surround it through an angle of 210°. To generate the x-ray focus, an electron beam is generated with an electron gun and the electron beam is directed over the target by suitable deflection. Such computed tomography systems can operate entirely without mechanically-rotating parts.

In another known embodiment of a computed tomography apparatus of the fifth generation as described in DE 40 15 105 C3, a target entirely enclosing the examination volume is used with a coaxial ring of electron sources is arranged close thereto. An x-ray focus rotating around the examination volume can likewise be generated by individual activation of the electron sources of the electron source ring.

U.S. Pat. No. 4,606,061 discloses a further embodiment of a computed tomography apparatus of the fifth generation in which an x-ray focus moving around the examination volume is generated on a target entirely enclosing the examination volume. An electron source ring coaxial to the target is provided that is activated for electron emission by a laser beam striking on its surface.

Due to the absence of a rotating x-ray tube, the aforementioned embodiments of computed tomography systems of the fifth generation achieve significantly higher scan speeds, but suffer from a reduced image quality and dose efficiency relative to computed tomography systems of the third generation. This is primarily a result of the limited possibilities for influencing beam parameters of the x-ray beam. In computed tomography systems of the third generation, a component known as a phi collimator is used that limits the aperture angle of the x-ray beam in the slice plane (X-Y plane) to the required FoV (Field of View). Unnecessary x-ray propagation outside of the region of interest, which leads to an increased scatter radiation and thus to a reduced image contrast and an increased radiation dose for the patient, is thereby avoided. In computed tomography systems of the fifth generation, no phi collimators are used due to the different technique for generation of the rotating x-ray focus. The same applies for filters for influencing the beam profile of the x-ray beam, for example a filter known as a bowtie filter that is arranged in front of the x-ray tube in computed tomography systems of the third generation. Such filters improve the dose efficiency by 15 to 20%, reduce the radiation dose for the patient, and prevent an over-exposure of the detector elements.

To improve the signal-to-noise ratio, scattered-ray grids to reduce the scatter radiation striking on the detectors are normally mounted on the incoming side of the x-ray detector. For an optimal suppression of the scatter radiation, the lamellae of such a scattered-ray grid should be aligned to the x-ray focus. In the known computed tomography systems of the fifth generation with a stationary scattered-ray grid, this cannot be realized with justifiable expense. The lamellae of the scattered-ray grid are therefore not aligned to the x-ray focus in the previously-described embodiments. In the known computed tomography systems of the fifth generation, the limitation of the x-ray beam in the Z-direction is achieved by a Z-collimator that is composed of two parallel, stationary rings that surround the examination volume within the target and detector ring, the rings therebetween defining the expansion of the x-ray beam in the Z-direction. Dependent on the mutual offset of the target and the x-ray detector in the Z-direction, this leads to a distortion of the ideally rectangular cross-section of the x-ray beam on the detector elements given the use of a multi-line detector, in particular to a banana-shaped or barrel-shaped distortion. FIG. 1 shows an example for a banana-shaped distortion of the cross-section 1 of the x-ray beam on an eight-line x-ray detector. The outer left detector lines 2 are not exposed in the center, or at least are less exposed in the center, while the outer right detector lines 2 are exposed only in the center. This banana-shaped beam profile on the detector can be avoided only when the Z-collimator is opened further, but this reduces the dose efficiency. If the Z-collimator is not opened as far, the outer detector channels are unusable since they detect no x-ray radiation or only very little x-ray radiation. This reduces the detector efficiency and the image quality and leads to increased partial volume effects.

SUMMARY OF THE INVENTION

An object of the present invention is to provide a computed tomography apparatus for fast image acquisition that provides an improved image quality relative to known computed tomography apparatus systems of the fifth generation.

The above object is achieved by an x-ray computed tomography apparatus having a stationary device for generating x-ray radiation from a target that at least partially encloses an examination volume of the apparatus in one plane. An x-ray focus moves around the examination volume is generated on the target, from which at least one x-ray beam is directed through the examination volume onto respective, momentarily opposite detector elements of a stationary x-ray detector that likewise at least partially surrounds the examination volume. Furthermore, one or more shaping elements for influencing one or more beam parameters of the x-ray beam are arranged between the target and the detector elements. One or more of these shaping elements is/are arranged on a carrier frame that can be rotated around a system axis of the examination volume in synchronization with the movement of the x-ray focus.

The x-ray computed tomography apparatus thus can be designed like the known computed tomography systems of the fifth generation with regard to the generation and the detection of the x-ray radiation, or designated for electron beam computed tomograph (EBCT). In contrast to conventional designs of such computed tomography systems, the inventive apparatus additionally has the aforementioned rotating carrier frame on which are arranged one or more shaping elements for influencing one or more beam parameters of the x-ray beam. The carrier frame that can be rotated around the system axis (z-axis) is moved in synchronization with the movement of the x-ray focus on the target. In this manner a scan speed is reached that is substantially increased relative to x-ray computed tomography systems of the third generation, since the carrier frame carries no heavy parts, in particular neither an x-ray tube nor the x-ray detectors. Relative to the carrier frame of a computed tomography apparatus of the third generation, the weight can be reduced by a factor of 100, such that a distinct increase in the rotation (and thus scan) speed can be achieved without reduction of the image quality. Moreover, a significant image improvement is achieved relative to known computed tomography systems of the fifth generation since the shaping elements rotating with the x-ray focus enable an optimal beam shaping and/or suppression of scatter radiation.

The synchronization between the movement of the carrier frame and the movement of the x-ray focus can ensue by synchronized activation of the actuator (drive) for the carrier frame and the device for generation of the x-ray radiation. Furthermore, a detection device can be provided on the carrier frame that detects the current position of the x-ray focus and transmits it to a control device that correspondingly regulates the movement of the carrier frame.

The forming elements for influencing one or more beam parameters of the x-ray beam can be fashioned and arranged such that they limit the aperture angle of the x-ray beam in the slice plane (X-Y plane; phi collimator), in the Z-direction (Z-collimator) or in both dimensions. Furthermore, these shaping elements can be fashioned as filters that influence the intensity profile of the x-ray beam or its spectral distribution. Finally, the shaping element can also form a scattered-ray grid for the x-ray detector.

In all cases, in the inventive computed tomography apparatus an optimal adaptation of the one or more shaping elements to the current x-ray focus is enabled since the shaping elements move in synchronization with the x-ray focus due to the rotating carrier frame. Moreover, the use of a phi collimator and/or bowtie filter is possible in this manner as with computed tomography systems of the third generation. The lamellae or walls of a scattered-ray grid arranged on the carrier frame can be optimally aligned to the x-ray focus. Both measures improve the image quality and reduce the x-ray radiation to which the patient is exposed. In this case, due to the rotation movement the individual cells of the scattered-ray grid also do not have to be adapted to the sub-division of the x-ray detector. Rather, the static relation between the scattered-ray grid and the x-ray detector can be utilized.

Given the arrangement of a Z-collimator on the carrier frame, a distortion of the projection of the x-ray beam on the detector surface can be prevented by suitable shaping of the lamellae of this Z-collimator. For this purpose, the borders of both limiting lamellae of the Z-collimator that are turned away from the x-ray focus can be adapted to the curve of the outer boundaries of the x-ray detector such that the projection edges of the x-ray beam on the detector surface follow this curve.

The light carrier frame in accordance with the invention can also be used for further improvement of a computed tomography apparatus as is known, for example, from U.S. Pat. No. 4,606,061. In this computed tomography apparatus, the moving x-ray focus is generated by a laser beam that strikes an electron source ring arranged at a slight distance from the annular target. There the laser beam produces electrons that are accelerated in the direction of the target by a voltage applied between the target and the electron source ring, and generate x-ray radiation at the target upon impact. The rotation of the focus around the examination volume is achieved by movement of the laser beam over the electron source ring that can be generated by a scan mechanism. In the present embodiment of such a computed tomography apparatus, the device for injecting (coupling) the laser beam into the electron source ring is also mounted on the carrier frame, in the simplest case a circular cover of the electron source ring with an injection window. In this manner it can be ensured that the laser beam always is incident at the correct position on the electron source ring. This reduces the danger of an error function or damage due to unwanted light reflections. In a version of this embodiment, a converging lens is arranged at the entrance window, with which the laser beam is additionally focused on the electron source ring. This increases the photo-emission efficiency.

In the inventive computed tomography apparatus, the device for generating the x-ray radiation as well as the x-ray detector can be fashioned as in the aforementioned computed tomography systems of the fifth generation. This also concerns the embodiment of the target as well as that of the detector unit, either as circular full rings or as partial-rings that extend by at least 180° around the examination volume. The detector ring and the target ring can be arranged coplanar or not coplanar in the same manner as in the prior art.

The light carrier frame used in the inventive computed tomography apparatus can be executed as an electrically passive element, such that no electrical signals or electrical power whatsoever must be transferred between the stationary parts of the computed tomography apparatus and the carrier frame. The rotation movement of the carrier frame is halted for the adjustment of the shaping elements, for example the change of the aperture width of the Z-collimator or to change a filter. The carrier frame is then brought into a specific angle or rotation position in which (in one embodiment) mechanical actuators can be connected at the stationary part with mechanical adjustment devices on the carrier frame, and a changed adjustment of the shaping elements can be effected by the mechanical actuators.

Both the scattered-ray grid and the collimators (phi and Z) are preferably mounted on the present carrier frame in accordance with the invention. Naturally, the computed tomography apparatus also can operate with only one of the specified shaping elements if it is sufficient for only some of the advantages to be achieved.

DESCRIPTION OF THE DRAWINGS

FIG. 7 shows an embodiment of a portion of a computed tomography apparatus according to a further embodiment of the present invention.

FIG. 8 is a detail view regarding the embodiment according to FIG. 7.

DESCRIPTION OF THE PREFERRED EMBODIMENTS

Figure 1:
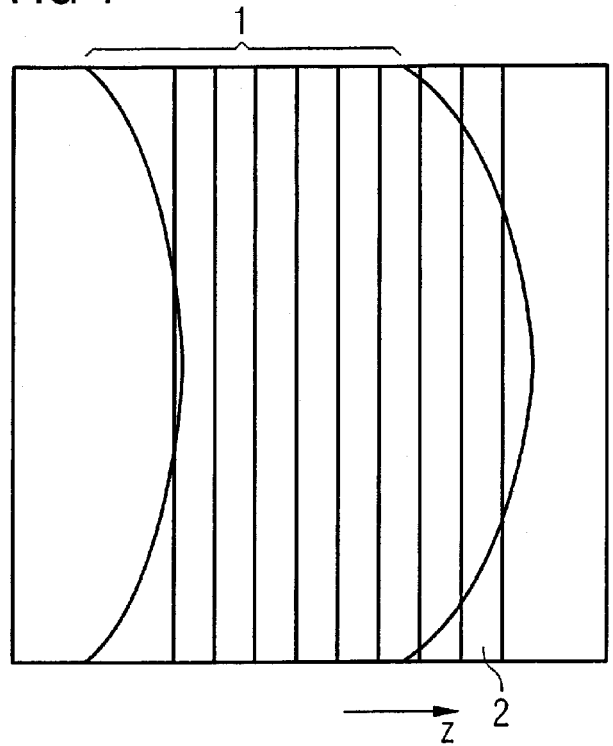
FIG. 1 schematically illustrates the distortion of the projections of the x-ray beam due to a stationary Z-collimator in known computed tomography systems of the 5th generation.

FIG. 1 was already explained in connection with the discussion of the prior art, and shows the banana-shaped distortion of the projection 1 of the x-ray beam on the detector lines 2 of an 8-line x-ray detector in known computed tomography systems of the 5th generation. This distortion materializes due to the annular Z-collimator used in these systems.

Figure 2:
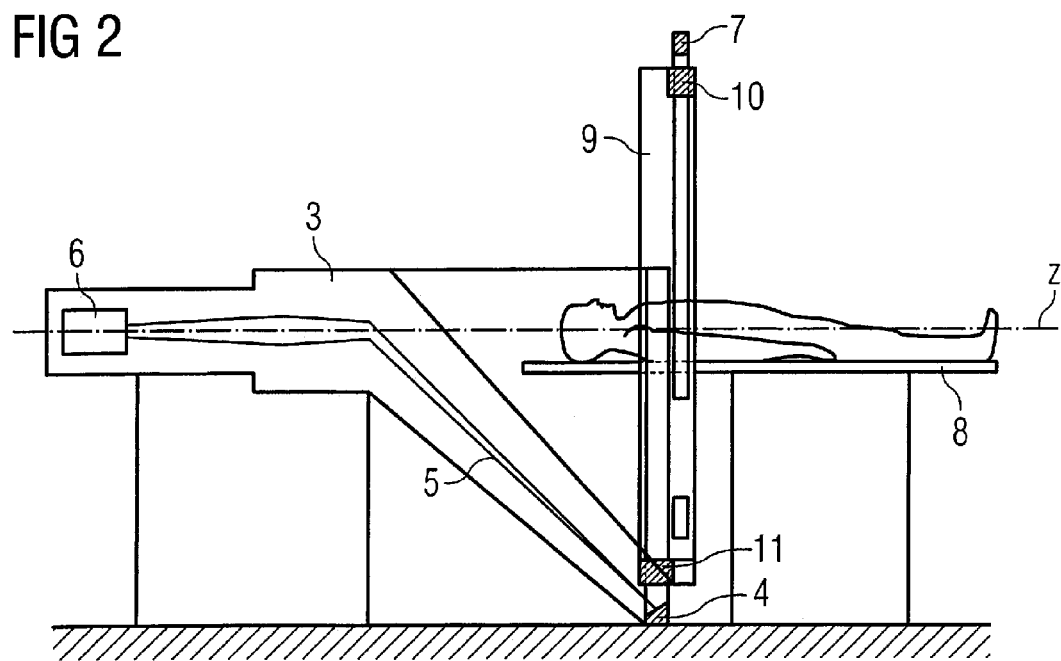
FIG. 2 schematically illustrates an example for the design of a computed tomography apparatus according to the present invention.

Such a distortion can be avoided with the inventive computed tomography apparatus by suitable shaping of the lamellae of the Z-collimator on the rotating carrier frame. FIG. 2 shows a schematic representation of an exemplary design of a computed tomography apparatus according to the present invention. In this example, the apparatus has an x-ray generating device 3 with a target 4 that extends as a partial ring through approximately 210° around the examination volume. The x-ray focus on the target 4 (which, for example, is composed of tungsten) is generated with an electron beam 5 that is focused from an electron gun 6 onto a point of the target 4 by various focusing and deflection devices. Via suitable deflection of the electron beam 5 over the partial ring of the target 4, an x-ray focus moving around the examination volume can be generated, from which the x-ray radiation emanates for irradiation of the subject. In the present example, no complete rotation occurs but rather only a partial rotation around the angle of 210°.

In the same manner, the x-ray detector 7 with one or more lines of detector elements extends parallel to the target 4 as a partial ring of 210° around the examination volume. The partial ring of the x-ray detector 7 is arranged relative to the target 4 such that each focus position on the target 4 lies opposite a detector element of the x-ray detector 7 relative to the examination volume. Both the target 4 and the x-ray detector 7 are stationary in this computed tomography apparatus.

An examination subject, for example a patient, is supported on the patient positioning table 8 and normally is moved at least partially along the z-axis during the image acquisition. A carrier frame 9 that can rotate around the z-axis, on which a scattered-ray grid 10 as well as (opposite to this) a phi and z-collimator 11 are mounted, extends around the examination volume. In the image acquisition, the rotation of the carrier frame 9 ensues in synchronization with the x-ray focus rotating on the target 4, such that the phi and z-collimator 11 is located in front of the x-ray focus and the scattered-ray grid 10 is located on the opposite side of the carrier frame 9 in front of the detector elements of the x-ray detector 7 on which the x-ray beam emanating from the x-ray focus directly strikes.

Figure 3:
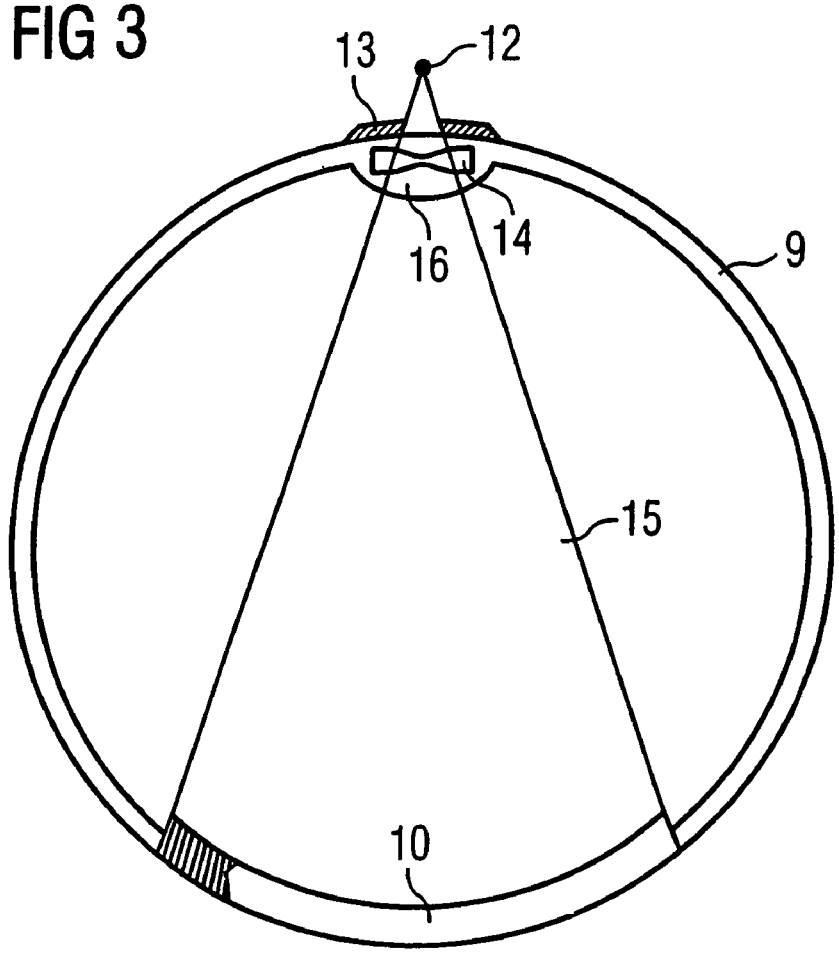
FIG. 3 shows an example for the arrangement of shaping elements on the rotatable carrier frame according to the present invention.

In a schematic representation, FIG. 3 shows an example for the rotatable carrier frame 9 viewed in the direction of the z-axis. In this example, an x-ray focus 12 is indicated on the target (not visible) from which x-ray radiation is emitted.

The phi collimator 13 can be seen on the carrier frame 9, the phi collimator limiting (in terms of the angle) the x-ray radiation emanating from the x-ray focus 12 in the slice plane, such that an x-ray beam 15 arrives in the examination volume with a defined aperture angle. A bowtie filter 14 that influences the intensity profile of the x-ray beam 15 in the slice plane is mounted below the phi collimator 13. Furthermore, one of the limitation lamellae of the Z-collimator 16 is shown in this figure that limits the spread of the x-ray beam 17 in the Z-direction. A scattered-ray grid 10 that is exactly aligned to the x-ray focus 12 is arranged opposite the collimators 13, 16. This is possible due to the carrier frame 9 rotating with the x-ray focus 12. The scatter radiation at the x-ray detector is distinctly reduced by this optimized scattered-ray grid 10, such that the image contrast is improved.

Figure 4:
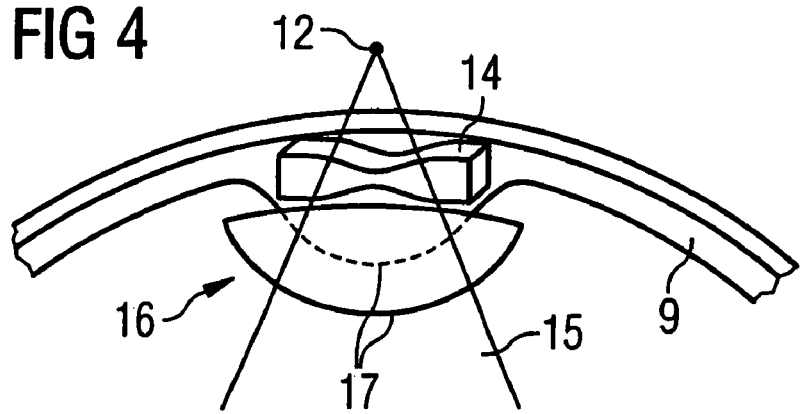
FIG. 4 is a perspective view of a portion of the inventive apparatus with the Z-collimator as well as the bowtie filter of FIG. 3.
Figure 5:
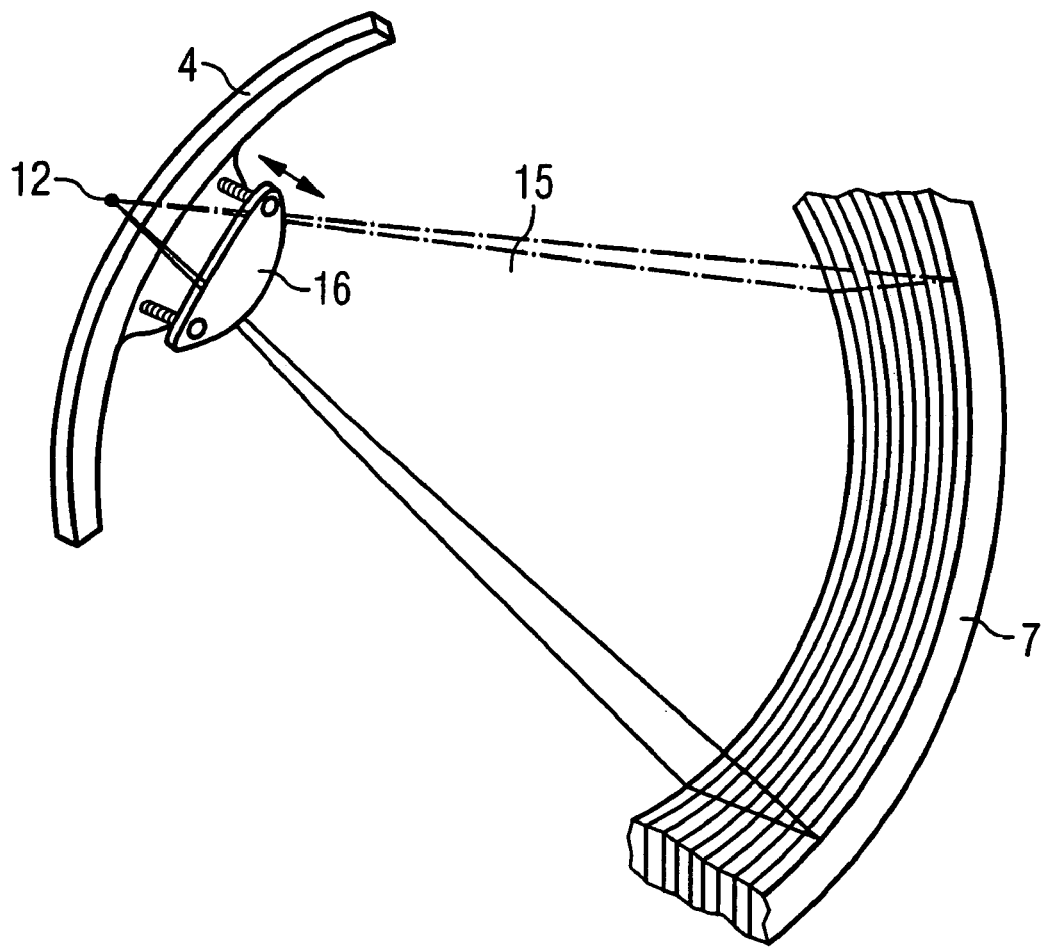
FIG. 5 shows the projection, adapted with the Z-collimator, of the x-ray beam on the detector in accordance with the invention.

To avoid a barrel-shaped or banana-shaped distortion of the projection of the x-ray beam on the detector surface, the limitation lamellae of the Z-collimator 16 can be adapted in terms of their shape to the projection geometry and the geometry of the detector. In a perspective partial view, FIG. 4 shows both lamellae 17 of the Z-collimator. Due to the arc-shaped formation it is achieved that the projection on the detector surface exactly follows the delimitations of the x-ray detector. The suitable shape of the individual lamellae can hereby be determined by calculation. FIG. 5, in which a displacement capability of the Z-collimator 16 in the Z-direction for adjustment of the width of the x-ray beam 15 in this direction is indicated, exemplarily shows this projection. By such an adaptation that is possible in the computed tomography of the invention, the dose efficiency as well as the detector efficiency is maximized and the image quality is improved.

Figure 6:
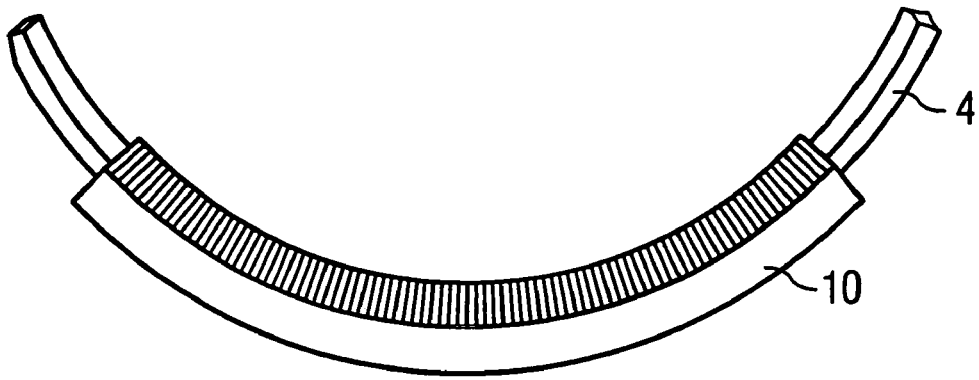
FIG. 6 is a perspective view of a portion of the apparatus with the scattered-ray grid of FIG. 3.

FIG. 6 shows an example for the design of the scattered-ray grid 10 according to FIG. 3 in a perspective representation.

FIGS. 7 and 8 show a further exemplary embodiment of a computed tomography apparatus according to the present invention, in which only the target 4, the x-ray detector 7 and the carrier frame 9 are shown in detail. The target 4 and x-ray detector 7 each, completely, annularly surround the examination volume. This embodiment concerns a computed tomography apparatus in which the electrons for the generation of the x-ray focus are produced by a laser beam 18 from an electron source ring 21 (made from a suitable, for example metallic or semiconducting material) operating as a cathode. For this purpose the laser beam is focused on the corresponding point of the electron source ring 21 that is only separated by a gap from the annular target 4 that forms the anode. The laser beam is thereby directed over the electron source ring 21 with a suitable scanner. Electrons that are accelerated toward the target 4 by the voltage between the electron source ring 21 and the target 4, and generate the desired x-ray radiation, are released at the corresponding point of the electron source ring 21 by the light effect. Details with regard to this type of generation of x-ray radiation can be learned from the aforementioned U.S. Pat. No. 4,606,061.

The ring of x-ray detector 7 likewise can be in FIG. 7.By means of the x-ray radiation generated at the x-ray focus, in connection with corresponding collimators an x-ray beam 15 is generated that strikes on the opposite detecter elements of the detector 7. In this example, the rotatable carrier frame 9 is also again provided with a scattered ray grid 10 as well as a Z- colliimator 16 that can be mechanically adjusted in terms of width. The inventive carrier frame 9 additionally has an iris viewing diaphragm 19 that, for the incident laser radiation 18, is opened by a window only at a point at which the x-ray focus should be directly generated. A collimator lens 20 via which the incident laser beam 18 is additionally focused on the electron source ring 21 is inserted into this window. FIG. 8 shows details of this arrangement.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray computed tomography apparatus comprising:
   a stationary x-ray generator having a target that at least partially surrounds an examination volume in a plane, said x-ray generator emitting an x-ray beam from a focus that moves around the examination volume on said target;
   a stationary x-ray detector that at least partially surrounds said examination volume, said stationary x-ray detector comprising a plurality of detector elements and said x-ray beam proceeding through said examination volume onto respective, momentarily opposite detector elements of said x-ray detector;
   a carrier frame carrying a Z-collimator that limits expansion of said x-ray beam in a direction along said system axis, said carrier frame being mounted to rotate around a system axis in synchronization with movement of said focus to maintain interaction between said at least one shaping element and said x-ray beam as said focus moves around said examination volume; and
   said Z-collimator comprising at least two parallel beam-limiting lamellae, between which said x-ray beam proceeds, said lamellae having respective edges each having a non-linear shape that, when projected onto the x-ray detector by the x-ray beam, produces a projected shape substantially coinciding with a side of said x-ray detector along said system axis.

2. x-ray computed tomography apparatus as claimed in claim 1 wherein said shaping element is a bowtie filter.

3. An x-ray computed tomography apparatus as claimed in claim 1 comprising a circular screen forming an electron source ring disposed on said carrier frame coaxially with respect to said target, said circular screen having a beam passage window for an optical beam proceeding to said electron source ring at one point.

4. An x-ray computed tomography apparatus as claimed in claim 3 comprising a beam collimating lens disposed in said beam passage window, which focuses said optical beam onto said electron source ring at said point.

* * * * *